（12）United States Patent
Rihan et al.

(10) Patent No.: US 8,474,324 B2
(45) Date of Patent: Jul. 2, 2013

(54) STRESS CORROSION CRACKING TESTING DEVICE

(75) Inventors: Rihan Omar Rihan, Dhahran (SA); Muwaffaq Qubbai, Dammam (SA); Mehaboob Basha, Dhahran (SA); Luai Al-Hadhrami, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 36 days.

(21) Appl. No.: 13/308,431

(22) Filed: Nov. 30, 2011

(65) Prior Publication Data

US 2013/0133434 A1 May 30, 2013

(51) Int. Cl.
*G01N 19/08* (2006.01)

(52) U.S. Cl.
USPC .......................................... 73/799

(58) Field of Classification Search
USPC .......................................... 73/700, 799, 803
See application file for complete search history.

(56) References Cited

U.S. PATENT DOCUMENTS

| | | | |
|---|---|---|---|
| 4,181,882 A * | 1/1980 | Isaacs et al. | 205/775.5 |
| 4,217,180 A | 8/1980 | Baxter et al. | |
| 4,335,615 A | 6/1982 | Kalfa | |
| 5,034,190 A | 7/1991 | Economy | |
| 5,254,310 A * | 10/1993 | Bressan | 422/53 |
| 5,370,799 A | 12/1994 | Oddo et al. | |
| 5,386,442 A | 1/1995 | Diaz et al. | |
| 5,517,851 A | 5/1996 | Berthold et al. | |
| 5,824,918 A * | 10/1998 | Zuk | 73/865.6 |
| 5,852,581 A * | 12/1998 | Beffa et al. | 365/201 |
| 5,901,071 A * | 5/1999 | Sakai et al. | 703/2 |
| 5,988,003 A * | 11/1999 | Zuk | 73/865.6 |
| 2011/0223672 A1 * | 9/2011 | Tumiatti et al. | 436/6 |

FOREIGN PATENT DOCUMENTS

| | | |
|---|---|---|
| EP | 1887341 A1 | 2/2008 |
| JP | 58168941 A | 10/1983 |
| JP | 58173451 A | 10/1983 |
| KR | 20080102710 A | 11/2008 |

OTHER PUBLICATIONS

R. Rihan, R.K. Singh Raman, and R. N. Ibrahim, "Circumferential Notched Tensile (CNT) Tests for Generating KIscc Data for Cast Iron Vessels Used in Hot Caustic Solutions", *International Journal of Pressure Vessels and Piping*, vol. 83, No. 5, pp. 388-393, (2006).

(Continued)

*Primary Examiner* — Max Noori
(74) *Attorney, Agent, or Firm* — Richard C. Litman

(57) ABSTRACT

The stress corrosion cracking (SCC) testing device includes a corrosion cell for placing a specimen to be tested therein. The corrosion cell is configured to simulate the extreme high temperature and pressure, as well as the corrosive environments experienced by engineered, industrial components. A heating element and a pressurizing assembly are operatively attached to the corrosive cell to simulate the high temperature and pressure environs. A circulation assembly is also attached to the corrosion cell to simulate both flowing and stagnant conditions of the corrosion solution that the industrial component can be subjected to. A loading assembly with a specimen holding shaft is operatively attached to the specimen to place a predetermined and constant tensile load on the specimen until fracture in order to determine $K_I$ and $K_{Iscc}$ of the engineered component. PTFE seals are used to seal the specimen holding shaft during testing.

16 Claims, 1 Drawing Sheet

OTHER PUBLICATIONS

R. Rihan, R.K. Singh Raman, and R.N. Ibrahim, "Determination of crack growth rate and threshold for caustic cracking (KIscc) of a cast iron using small circumferential notched tensile (CNT) specimens", *Materials Science and Engineering: A*, vol. 425, No. 1-2, pp. 272-277, (2006).

R.K. Singh Raman, R. Rihan, and R.N. Ibrahim, "A Novel Approach to the Determination of Threshold for Stress Corrosion Cracking (KIscc) Using Round Tensile Specimens", *Materials Science and Engineering: A*, vol. 452-453, pp. 652-656, (2007).

R.K. Singh Raman, R. Rihan, and R.N. Ibrahim, "Validation of a Novel Approach to Determination of Threshold for Stress Corrosion Cracking (KIscc)", *Materials Science and Engineering: A*, vol. 452-453, pp. 652-656, (2007).

\* cited by examiner

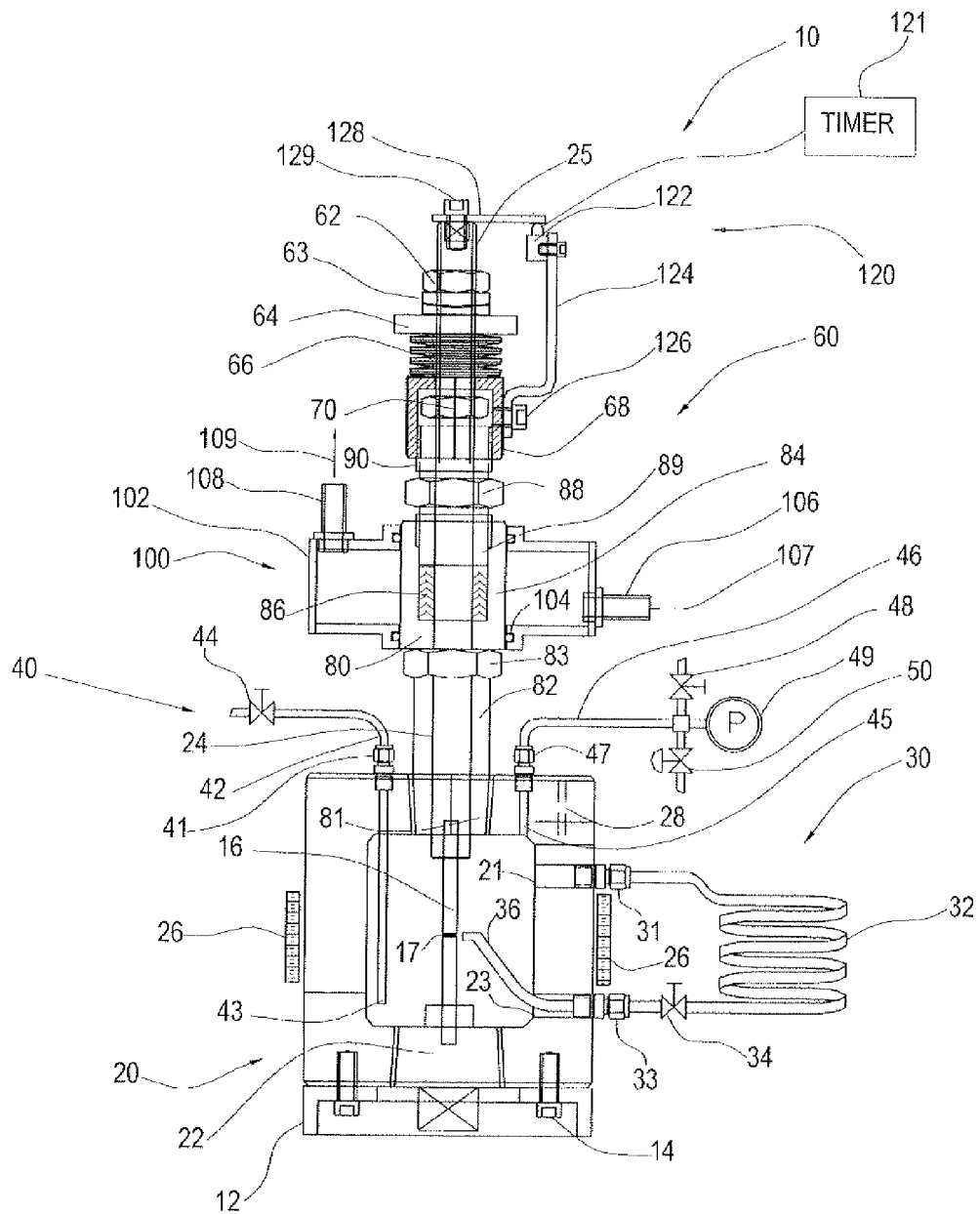

STRESS CORROSION CRACKING TESTING DEVICE

BACKGROUND OF THE INVENTION

1. Field of the Invention

The present invention relates to testing devices, and particularly to a stress corrosion cracking testing device that is capable of testing engineering materials, particularly normally ductile and brittle metals for failure due to stress corrosion cracking (SCC) at high temperature and high pressure.

2. Description of the Related Art

Stress corrosion cracking refers to the sudden failure of structural materials, such as normally ductile and brittle metals and metal alloys, under conditions in which the structural material is subject to tensile stress in a corrosive environment. Stress corrosion cracking (SCC) is considered to be one of the most dangerous forms of failure due to the typical locations at which such failures can occur and the potentially devastating impact therefrom. SCC of in-service components can occur in areas that are undetectable and difficult to access. Due to the inconspicuous nature of these occurrences, sudden failure of the component(s) is often accompanied by catastrophic results. In order to counter such potential dangers, a complete shutdown may be necessary for maintenance and repair. Such actions can incur prohibitive costs, both from loss of production and the maintenance that may be required.

Due to the above, engineers and designers must carefully assess various different materials to be used in making the components for an industrial environment. At the very least, it is importance to accurately determine the stress intensity factor ($K_I$) and the threshold stress intensity ($K_{Iscc}$) in the components made from those materials in order to determine the life expectancy of the component in corrosive environments, conformance to construction standards, and the ability of the component to meet performance demands.

Various different techniques and testing apparatus/rigs have been developed to address this issue. A typical testing unit involves the use of a specimen placed in a rig and exposed to tensile stress. Measurements are taken to determine $K_I$ and $K_{Iscc}$. However, the inventors are not aware of any testing devices that assess SCC at extreme conditions, such as at very high pressures and temperatures actually experienced by components in an industrial setting. Moreover, the majority of these testing rigs tend to be bulky, requiring relatively large amounts of space, and the testing rigs are expensive, both in terms of the device itself and the necessary upkeep and specialty needs. In addition, the conventional fracture specimens used for testing, such as compact tension (CT) and pre-cracked double cantilever beam (DCB) specimens, are relatively expensive and bulky, requiring a rather large thickness in order to achieve plane strain conditions. In some situations, those types of specimens cannot be obtained from failed components.

In light of the above, it would be a benefit in the art of materials testing to provide a testing device that is relatively inexpensive and compact and can provide SCC performance data for materials that will be exposed to extreme or high temperatures, high pressures, and corrosion. Thus, a stress corrosion cracking testing device solving the aforementioned problems is desired.

SUMMARY OF THE INVENTION

The stress corrosion cracking (SCC) testing device includes a corrosion cell for placing a specimen to be tested therein. The corrosion cell is configured to simulate the extreme high temperature and pressure and corrosive environments experienced by engineered, industrial components. A heating element and a pressurizing assembly are operatively attached to the corrosive cell to simulate the high temperature and pressure conditions. A circulation assembly is also attached to the corrosion cell to simulate both flowing and stagnant conditions of the corrosion solution that the industrial component can be subjected to. A loading assembly with a specimen holding shaft is operatively attached to the specimen to place a predetermined and constant tensile load on the specimen till fracture in order to determine $K_I$ and $K_{Iscc}$ of the engineered component. PTFE (polytetrafluoroethylene) seals are used to seal the specimen holding shaft during testing, and a cooling assembly is provided to maintain the seal at safe operative levels. A timing assembly is also provided to determine the time interval of failure.

These and other features of the present invention will become readily apparent upon further review of the following specification and drawings.

BRIEF DESCRIPTION OF THE DRAWINGS

The sole drawing FIGURE is a side view in section of a stress corrosion cracking testing device according to the present invention.

Similar reference characters denote corresponding features consistently throughout the attached drawings.

DETAILED DESCRIPTION OF THE PREFERRED EMBODIMENTS

The stress corrosion cracking testing device, generally referred to in the drawing as reference number 10, is configured as a relatively simple, fast and cost effective means of determining the susceptibility of engineering materials at flowing solution and high temperatures and pressures to SCC. As shown in the FIGURE, the stress corrosion cracking testing device 10 includes a support base 12 and a corrosion cell 20 mounted thereon with fasteners 14. In the non-limiting exemplary embodiment, the corrosion cell 20 can be a substantially rectangular, square or cylindrical, hollow block constructed from high corrosion resistant alloys. Some examples of such alloys include, but not limited to, 316 stainless steel and high-nickel alloys, e.g., Hastelloy 0276, Monel 400, and Inconel 600. The corrosion cell 20 is configured to house the specimen 16 and to simulate the corrosive environment present in industry equipment and components, such as reactors, pressure vessels, and pipelines.

The specimen 16 is preferably a circumferentially notched tensile (CNT) specimen. In comparison with other fracture mechanics specimens, such as compact tension (CT) and pre-cracked double cantilever beam (DCB) specimens that have been used by researchers, the CNT specimen 16 is much less expensive and smaller. The other types of specimens mentioned above tend to be expensive and bulky, and require a large thickness in order to achieve plane strain conditions. Moreover, in some instances, CT or DCB specimens cannot be obtained from a failed component, such as when testing a small component for failure analysis. In contrast, the CNT specimen 16 can be obtained from a failed component of various sizes, and the CNT specimen can be stressed to achieve plane strain conditions and low plasticity, despite the small size.

The specimen 16 is held at one end by a specimen holding nut 22. The holding nut 22 includes threads for holding the one end of the specimen 16. Preferably, the specimen holding nut 22 is threaded according to National Pipe Taper (NPT)

standards for mounting the specimen 16 into the corrosion cell 20. The nut 22 also seals the bottom of the corrosion cell 20. The opposite end of the specimen 16 is held by a specimen holding shaft 24, which is operatively attached to the tensile loading assembly 60, the details of which will be described below.

In order to simulate the extreme high temperatures, the stress corrosion cracking testing device 10 includes at least one heating element 26 disposed around the corrosion cell 20. The heating element 26 can be a controlled electric band heater that can heat the corrosive solution contained therein to temperatures up to 360° C. Other similar heaters can also be used to heat the solution. Such temperatures are exemplary of some of the extreme temperatures experienced by industrial components, which gives rise to potential component failure. The temperatures can be monitored and recorded by a thermocouple 28 disposed inside a corresponding aperture in the body of the corrosion cell 20.

In addition to high temperatures, industrial components can be subjected to both stagnant and flowing corrosive solution during operation. To simulate flow, the stress corrosion cracking testing device 10 includes a circulation assembly 30 detachably mounted to a side of the corrosion cell 20. The circulation assembly 30 includes a circulation tube 32 having an inlet end mounted by a fastener or fitting 31 to a corresponding port or bore 21 in the side of the corrosion cell 20. The opposite, outlet end of the tube 32 is connected to a corresponding port or bore 23 by another fastener or fitting 33. Both fasteners 31, 33 seal their respective connections. The circulation of the corrosive solution through the interior chamber of the corrosion cell 20 is facilitated by natural convection as a result of the large difference in temperature between the corrosion cell (high temperature) and the circulation tube 32 (low temperature). The outlet of the circulation tube 32 can include an isolating outlet or extension 36 configured to closely focus the outlet flow stream towards the circumferential notch 17 on the specimen 16, as shown in the drawing, the notch 17 being the critical region for testing SCC. In addition to the above, the circulation assembly 30 can include a check or isolating valve 34 in order to selectively meter or completely shut off circulation for those instances when it is desired to perform SCC tests in stagnant solution flow conditions.

In order to simulate the high pressures, the SCC testing device 10 includes a pressurizing assembly 40. The pressurizing assembly 40 includes a gas inlet 42 connected to an inlet fastener or fitting 41. The gas inlet 42 can be a tube configured to handle the pressures and the chemical effects, if any, of the gas. The fastener 41 seals the connection between the gas inlet 42 and the interior of the corrosion cell 20. The gas inlet side of the pressurizing assembly 40 can include an elongate, inlet tube or cylinder 43 in communication with the gas inlet 42 through a corresponding port or bore in the corrosion cell 20. The inlet tube 43 can extend towards the bottom of the interior chamber in order to allow efficient distribution of the pressurizing gas. Moreover, the inlet tube 43 can be provided with a porous element, similar to a dispersion stone, which will create bubbles for more efficient distribution of the gas. A gas inlet valve 44 can be operatively attached to the gas inlet 42 for selectively controlling the operation and rate of pressurizing gas flow into the interior chamber. During operation, the pressurizing assembly 40 can pressurize the corrosion cell 20 up to 200 bar, providing a pressure range in which actual industrial components operate.

The pressurizing gas is allowed to escape through an outlet tube 45 extending from the corrosion cell 20. The outlet tube 45 is operatively attached to a gas outlet 46 via an outlet fastener or fitting 47, which provides a sealed connection therebetween. It is to be noted that all the fasteners mentioned above can be compression type fasteners constructed from high corrosion-resistant alloys, such as 316 stainless steel or high-nickel alloys, in order to compensate for the high pressure/temperature and corrosive operating environment. The gas outlet 46 can be a tube constructed in substantially the same manner as the gas inlet 42. The gas outlet 46 can include a gas outlet 48 operatively attached thereto for selective control of gas outlet flow. A pressure gauge 49 attached to the gas outlet 46 measures and monitors pressure inside the corrosion cell 20. If the pressure exceeds a predetermined safe limit, a safety or pressure relief valve 50 attached to the gas outlet 46 permits automatic release of gas to relieve the pressure. The pressurizing gas may be compressed air, an insert gas, or if greater cooling is needed, supercritical carbon dioxide or nitrogen.

The tensile force for inducing stress cracking in the specimen 16 is provided by a tensile loading assembly 60. As shown in the FIGURE, the tensile loading assembly 60 includes one end of the specimen holding shaft 24 threaded onto one end of the specimen 16. The specimen holding shaft 24 includes a threaded portion 25 at the opposite end. The bottom portion of the threaded end 25 is surrounded by a safety cap 68, and a safety nut 70 is disposed onto threads beneath the safety cap 68. The safety nut 70 can be adjusted up or down along the threaded end 25 of the specimen holding shaft 24, as required by the user. The safety nut 70 serves as a stop to prevent the specimen holding shaft 24 from being ejected as a projectile when the specimen 16 breaks by allowing the safety nut 70 to abut against the underside of the safety cap 68 and stop further movement during the break. The safety cap is rigidly fixed in position, and the specimen holding shaft is slidably through the cap 68.

The actual tensile force can be provided by a biasing means in the form of a plurality of Belleville washer springs 66 disposed between a loading bracket or frame 64 and the safety cap 68. The washer springs 66 are used to exert a certain constant tensile load on the specimen 16. In operation, an external loading device or means is forced against the loading bracket 64 to compress or load the washer springs 66 to a desired depth or amount of stored energy. Once loaded, an adjustment nut 62 mounted above the loading bracket 64 is adjusted to set and hold the loading bracket 64 in position. Then the external load is removed. The removal of the external load allows the stored energy in the springs 66 to be transmitted to the specimen 16 as a tensile load by biasing the loading bracket 64, which the specimen holding shaft 24 is rigidly attached to, upward, thereby stretching the specimen 16. In order to insure that the tensile load is maintained axially, the tensile loading assembly 60 also includes self-alignment washers 63 disposed between the adjustment nut 62 and the loading bracket 64.

During the testing stage of the SCC testing device 10, the testing device 10 must be sealed as a matter of safety, since the corrosion cell 20 functions similar to a pressure vessel, and measures must be taken to prevent inadvertent harm from accidentally released corrosive solution and the high temperatures thereof. In order to seal the testing system 10, the SCC testing device 10 includes a seal assembly 80 slidably engaged with the specimen holding shaft 24. The seal assembly 80 includes a lower, attachment sleeve or tube 82 for mounting the seal assembly 80 onto the top portion of the corrosion cell 20, and an upper seal housing 84. The attachment sleeve 82 can be a substantially cylindrical tube having a threaded, tapered end 81 and a hollow interior accommodating the specimen holding shaft 24 for reciprocating movement therein. The threaded end 81 seals the upper portion of the corrosion cell 20, and also mounts the seal assembly 80 thereon. The threaded engagement is preferably in accord with NPT standards. The seal assembly 80 can be provided with a hexagonal head 83 between the seal housing 84 and the attachment sleeve 82 (which are one solid piece) to allow the use of a spanner or wrench for threading the seal assembly 80 onto the corrosion cell 20.

The upper, seal housing 84 includes a hollow, interior chamber for housing or holding a plurality of seals 86 stacked atop each other. The seals 86 can be a plurality of polytetrafluoroethylene (PTFE) annular rings having a V-shaped cross section, or may be PTFE vee packings. PTFE exhibits excellent sealing characteristics and is highly resistant to corrosion.

In order to insure that the seals 86 engage the specimen holding shaft 24 properly to seal the same, the sealing assembly 80 includes a seal packing nut 88 threadably mounted above the seal housing 84. A packing cylinder 89 is disposed below the seal packing nut 88. The packing cylinder 89 can be either integral with or separate from the seal packing nut 88. Selective operation of the sealing nut 88 raises or lowers the sealing nut 88 with respect to the seal housing 84. In typical use, the sealing nut 88 is lowered so that the packing cylinder 89 compresses the stacked, V-shaped seals 86 until the proper or desired seal around the specimen holding shaft 24 has been obtained. The upper end of the seal assembly 80 above the seal packing nut 88 includes a mounting boss 90 for mounting the safety cap 68 thereon.

While PTFE exhibits excellent corrosion resistance to almost all chemicals, it is not recommended to be used in environments above 260° C., a requirement that is much less than the extreme testing conditions of up to 360° C. In order to compensate, the sealing point, i.e., the seal housing 84, is placed above the corrosion cell 20, and the SCC testing device 10 includes a cooling assembly 100 for cooling the seals 86.

As shown in the drawing FIGURE, the cooling assembly 100 surrounds the seal housing 84. The cooling medium is preferably circulating water. To facilitate water circulation, the cooling assembly 100 includes a housing 102 surrounding the seal housing 84. The housing 102 includes a hollow chamber for holding and circulating the water therein. O-ring seals 104 can be provided to seal and prevent leaks. One side of the housing 102 includes an inlet port connector 106 configured to be connected to a source of cooling water inlet 107. Another side of the housing 102 includes an outlet port connector 108 configured to be attached to a tube or similar means permitting flow of the circulating water through an outlet 109. Thus, the water enters the housing 102 through the inlet port connector 106 and circulates around the seal housing 84 to cool the seals 86 inside the seal housing 84. The heated water exits through the outlet port connector 108 to be recirculated through the cooling assembly 100 or further processed. If more aggressive measures are required, the cooling assembly 100 can include a cooling element directly connected to the housing 102 or the cooling water outlet 109 for better control of the water temperature. In the latter case, the heated water from the cooling water outlet 109 can be cooled down to desired temperatures and circulated back through the cooling water inlet 107 in an efficient closed-loop system.

In order to monitor and measure the time duration between load and stress failure of the specimen 16, the SCC testing device 10 includes a timing assembly 120. The timing assembly 120 includes a micro switch 122 attached to a mounting bracket 124. The mounting bracket 124 is secured to the safety cap 68 by a fastener 126. The micro switch 122 is electrically connected to a timer 121, and the timer 121 measures the time interval between the closed circuit state and the open circuit state of the micro switch 122. As shown, a contact arm 128 is attached to the distal end of the specimen holding shaft 24. The contact arm 128 is held in place by a fastener 129. During the experiment and before the specimen breaks, the electrical circuit is maintained in a closed state by having the contact arm 128 in contact with the micro switch 122. When the specimen 16 breaks, the loading bracket 64 moves up, which in turn, correspondingly moves the contact arm 128 upward to thereby break contact with the micro switch 122 and open the circuit. Thus, the time to failure can be determined by measuring the interval between load release and specimen failure.

As can be seen from the drawing FIGURE, the SCC testing device 10 is a relatively simple mechanical device. The testing device 10 is a relatively fast and cost-effective means for determining the susceptibility of engineering materials exposed to corrosion and high temperatures and pressures to SCC. The compact size of the SCC testing device 10 allows it to be placed on desks, tables, or shelves with minimal footprint and hazards.

It is to be understood that the SCC testing device 10 encompasses a variety of alternatives. For example, the cooling assembly 100 can utilize other coolants, such as antifreeze, for higher heat transfer capacity. Alternative springs, such as coil springs, leaf springs, electromagnetic springs, and other biasing means can also be used to apply the constant tensile force.

It is to be understood that the present invention is not limited to the embodiments described above, but encompasses any and all embodiments within the scope of the following claims.

We claim:

1. A stress corrosion cracking (SCC) testing device, comprising:
    a base;
    a corrosion cell mounted to the base, the corrosion cell having a hollow interior chamber adapted for holding a circumferentially notched tensile specimen for SCC testing and a solution of a corrosive substance therein;
    at least one heating element surrounding the corrosion cell, the at least one heating element being selectively actuated to heat the interior of the corrosion cell up to 360° C.;
    a circulation assembly operatively attached to a side of the corrosion cell, the circulation assembly being selectively operable to induce both stagnant and flow states of the corrosive solution disposed in the corrosion cell;
    a pressurizing assembly operatively attached to the corrosion cell, the pressurizing assembly being adapted for admitting a pressurized gas into the corrosion cell to pressurize the corrosion cell up to 200 bar;
    a tensile loading assembly adapted for coupling to the specimen inside the corrosion cell, the tensile loading assembly being configured to apply a constant tensile load on the specimen until the specimen breaks to thereby determine at least the stress intensity factor ($K_I$) and the threshold stress intensity ($K_{Iscc}$);
    a sealing assembly disposed between the loading assembly and the corrosion cell, the sealing assembly having a plurality of corrosion resistant seals for preventing leakage of the corrosive solution at high temperatures and pressures;
    a cooling assembly mounted to the sealing assembly for cooling the seals in the sealing assembly; and a timing assembly operatively attached to one end of the tensile loading assembly, the timing assembly monitoring and measuring the time interval for the specimen to break under load.

2. The stress corrosion cracking testing device according to claim 1, wherein said corrosion cell has a bottom surface having a specimen holding nut mounted thereon adapted for holding a threaded lower end of the specimen, and said tensile loading assembly comprises a specimen holding shaft having a lower end adapted for holding an upper end of the specimen.

3. The stress corrosion cracking testing device according to claim 2, wherein said specimen holding shaft has a threaded upper end, said tensile loading assembly further comprising:
   a safety cap rigidly fixed in position, said specimen holding shaft being slidable through the safety cap;
   a safety nut threadably engaged with the threaded upper end beneath the safety cap, the safety nut being adjustable along the threaded upper end and serving as an abutment to stop movement of the specimen holding shaft when said specimen breaks during testing by abutting against an undersurface of the safety cap;
   a loading bracket disposed above the safety cap, the loading bracket being rigidly attached to the upper end of the specimen holding shaft;
   at least one spring disposed between the loading bracket and the safety cap, the at least one spring biasing the loading bracket upward to exert a tensile load on the specimen; and
   an adjustment nut disposed above the loading bracket and threaded onto the upper end of said specimen holding shaft, the adjustment nut being selectively raised and lowered to adjust the tensile load on the specimen.

4. The stress corrosion cracking testing device according to claim 3, wherein said at least one spring comprises a plurality of Belleville washers.

5. The stress corrosion cracking testing device according to claim 3, further comprising a plurality of self-alignment washers disposed between said adjustment nut and said loading bracket to insure that said tensile load is maintained axially.

6. The stress corrosion cracking testing device according to claim 3, wherein said timing assembly comprises:
   a mounting bracket secured to said safety cap;
   a micro switch attached to the mounting bracket;
   a timer operatively connected to the micro switch; and
   a contact beam mounted to the upper end of said specimen holding shaft, the contact beam being in selective contact with the micro switch, said contact beam normally being in contact with the micro switch to turn the timer on to measure failure time, contact between the contact beam and the micro switch being broken to stop the timer at the failure time when said to specimen fails, raising said specimen holding shaft.

7. The stress corrosion cracking testing device according to claim 1, wherein said corrosion cell is constructed from highly corrosion-resistant alloys.

8. The stress corrosion cracking testing device according to claim 1, wherein said at least one heating element comprises a controlled electric band heater.

9. The stress corrosion cracking testing device according to claim 8, wherein said corrosion cell has a recess defined therein, the testing device further comprising a thermocouple disposed in the recess in said corrosion cell, the thermocouple monitoring and measuring temperature in said corrosion cell.

10. The stress corrosion cracking testing device according to claim 1, wherein said corrosion cell has an inlet port and an outlet port, said circulation assembly comprising:
   a fitting disposed in the inlet port and a fitting disposed in the outlet port, the fittings each having a seal;
   a circulation tube having an inlet end and an outlet end, the inlet end being connected to the fitting on the inlet port and the outlet end being connected to the fitting on the outlet port; and
   a valve attached to the circulation tube, the valve being selectively actuated to allow circulation flow of the corrosive solution to simulate a circulating corrosive solution, and being selectively actuated to completely shut off flow into and out of said corrosion cell to induce a stagnant state for the corrosive solution.

11. The stress corrosion cracking testing device according to claim 10, further comprising an isolating outlet attached to said outlet port inside said corrosion cell, the isolating outlet focusing outlet flow towards a circumferential notch defined in the specimen.

12. The stress corrosion cracking testing device according to claim 1, wherein said pressurizing assembly comprises:
   a gas inlet tube having an inlet valve, the gas inlet tube extending into said corrosion cell, the gas inlet tube being adapted for connection to a source of pressurized gas;
   a gas outlet tube extending from said corrosion cell, the outlet tube having an outlet valve;
   a pressure gauge attached to the gas outlet tube to measure and monitor pressure inside said corrosion cell; and
   a pressure relief valve attached to the gas outlet tube, the pressure relief valve automatically opening to relieve pressure when a predetermined safe pressure limit has been exceeded.

13. The stress corrosion cracking testing device according to claim 1, wherein said sealing assembly comprises:
   an attachment sleeve slidably engaged with said specimen holding shaft, the attachment sleeve mounting the whole sealing assembly onto a top portion of said corrosion cell in a sealed manner;
   a seal housing slidably engaged with said specimen holding shaft, the seal housing being disposed on top of the attachment sleeve, the seal housing having an interior chamber, said plurality of seals being disposed in the interior chamber;
   a seal packing nut threadably and rotatably mounted above the seal housing;
   a packing cylinder disposed below the seal packing nut, the packing cylinder being in engagement with said plurality of seals; and
   a mounting boss disposed above the seal packing nut, the mounting boss facilitating mounting of said safety cap thereon;
   wherein selective rotation of the seal packing nut causes the packing cylinder to move away or press down on said plurality of seals to insure a proper seal is maintained against said specimen holding shaft.

14. The stress corrosion cracking testing device according to claim 13, wherein said plurality of seals comprises a plurality of PTFE annular rings having a V-shaped cross section.

15. The stress corrosion cracking testing device according to claim 14, wherein said cooling assembly comprises:
   a housing surrounding said seal housing, the housing having a hollow interior chamber for holding and circulating a cooling medium therein and seals to prevent leakage of the cooling medium;
   an inlet port connector disposed on one side of the housing, the inlet port connector being configured to be connected to a source of the cooling medium; and an outlet port connector disposed on another side of the housing, the outlet port connector permitting flow of the cooling medium out of the housing.

16. The stress corrosion cracking testing device according to claim 14, wherein said cooling medium comprises water.

* * * * *